United States Patent

Wingert et al.

Patent Number: 6,133,468
Date of Patent: Oct. 17, 2000

[54] METHOD FOR PREPARING SUBSTITUTED BENZYL BROMIDES

[75] Inventors: Horst Wingert, Mannheim; Norbert Götz, Worms; Michael Keil, Freinsheim; Bernd Müller, Frankenthal, all of Germany

[73] Assignee: BASF Aktiengesellschaft, Ludwigshafen, Germany

[21] Appl. No.: 09/462,630

[22] PCT Filed: Jul. 20, 1998

[86] PCT No.: PCT/EP98/04485

§ 371 Date: Jan. 11, 2000

§ 102(e) Date: Jan. 11, 2000

[87] PCT Pub. No.: WO99/06339

PCT Pub. Date: Feb. 11, 1999

[30] Foreign Application Priority Data

Jul. 30, 1997 [DE] Germany .......................... 197 32 693

[51] Int. Cl.⁷ .......................... C07C 255/00; C07C 69/76; C07C 22/00; C07C 17/00
[52] U.S. Cl. ............................. 558/425; 560/8; 570/185; 570/196
[58] Field of Search .................... 570/185, 196; 560/8; 558/425

[56] References Cited

FOREIGN PATENT DOCUMENTS

| | | |
|---|---|---|
| 336 567 | 10/1989 | European Pat. Off. . |
| 553 879 | 8/1993 | European Pat. Off. . |
| 27 14 485 | 10/1976 | Germany . |
| 633 765 | 12/1982 | Switzerland . |
| 707990 | 4/1954 | United Kingdom . |

OTHER PUBLICATIONS

Patent Abstracts of Japan, vol. 014, No. 531 (C–0780), 1990.
Houben–Weyl, vol. 5/4, pp 334–336, 1960 with translation.

*Primary Examiner*—Joseph K. McKane
*Assistant Examiner*—Joseph Murray
*Attorney, Agent, or Firm*—Keil & Weinkauf

[57] ABSTRACT

Substituted benzyl bromides of the formula I

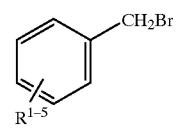

where at least one substituent $R^{1-5}$ is an electron-attracting group such as fluorine, chlorine, bromine, $C_1$–$C_4$-alkoxycarbonyl, cyano or nitro, and the other substituents $R^{1-5}$ are hydrogen or methyl,
are prepared by bromination of substituted toluenes of the formula II

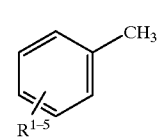

with a brominating agent at from 20 to 95° C.

6 Claims, No Drawings

METHOD FOR PREPARING SUBSTITUTED BENZYL BROMIDES

This Application is a 371 of PCT/EP98/04485 filed Jul. 20, 1998.

The present invention relates to a process for preparing substituted benzyl bromides of the formula I

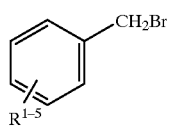

where at least one substituent $R^{1-5}$ is an electron-attracting group such as fluorine, chlorine, bromine, $C_1$–$C_4$-alkoxycarbonyl, cyano or nitro, and the other substituents $R^{1-5}$ are hydrogen or methyl,
by bromination of substituted toluenes of the formula II

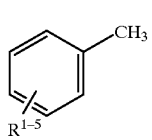

with a brominating agent at from 20 to 95° C.

Side-chain bromination of alkylaromatic compounds has been known for a long time (Houben-Weyl, Volume 5/4, pages. 331 et seq. (1960)).

It is pointed out in this review that electron-attracting substituents, such as halogen atoms or nitro groups, make this reaction difficult. Compounds which can be substituted only with great difficulty, specifically nitrotoluenes, can often be induced to react only at temperatures above 100° C. and under pressure, which involves considerable safety problems because of the low thermal stability of the compounds.

There is a description in more recent literature (EP-A 336 567) of the particularly difficult preparation of o-nitrobenzyl bromide by bromination of o-nitrotoluene with hydrogen bromide in the presence of hydrogen peroxide while irradiating with light, it having been possible to obtain selectivities of more than 90%. This process has been found to have the following disadvantages:

The bromine free radicals which are required are generated by irradiating with light which, on continuous operation, may result in coating of the lamps and thus considerable adverse effects.

Achieving the optimum depends on maintaining the narrow temperature range of 60–70° C. Good selectivities are obtained only with relatively low conversions.

For optimal reaction conditions, the hydrogen peroxide/substrate molar ratio and the hydrogen peroxide/hydrogen bromide molar ratio can be varied only within relatively narrow limits.

It has now been found that benzyl bromides substituted by electron-attracting groups are obtained with very good selectivities when the bromination is carried out in the presence of an azo carbonitrile or of an azo carboxylic ester and in the presence of an oxidizing agent.

It is surprising that it is possible to generate bromine free radicals using organic initiators even in the presence of strong oxidizing agents. Azo carboxylic esters and azo carbonitriles are particularly stable in the presence of said oxidizing agents and are therefore predestined for use as initiators in the novel process. The novel process has a number of industrial and economic advantages which are briefly listed below and are explained in detail hereinafter:

1. Omission of the elaborate apparatus needed for the irradiation
2. Possibility of wide variation of the brominating and oxidizing agents used
3. Temperature window wider and extending to lower reaction temperatures
4. The sequence of the addition of the individual reactants can be reversed. The brominating agent is metered into a mixture of the substrate to be brominated and the oxidizing agent. The concentration of corrosive brominating agent, especially hydrogen bromide, in the reaction vessel can be kept very low in this way.

Solvents suitable for the novel process are those which are inert during the bromination, for example aromatic hydrocarbons such as benzene, tert-butylbenzene and tert-amylbenzene, halogenated hydrocarbons such as methylene chloride, chloroform and chlorobenzene, 1,2-dichloroethane, tetrachloromethane, dichlorobenzene or trichlorobenzene. It is also possible to use mixtures of said solvents.

Halogenated hydrocarbons such as methylene chloride, 1,2-dichloroethane, chloroform, tetrachloromethane, ortho- or para-dichlorobenzene, 1,2,4-trichlorobenzene and, in particular, chlorobenzene are preferred.

The ortho-nitrotoluenes II employed in the novel process can in most cases be purchased or are easily obtainable by processes described in the literature (eg. Organikum, Barth Verlagsgesellschaft (1993) 320 et seq.).

In contrast with the disclosure in EP-A 336 567, the procedure for the novel process is very flexible. It is possible to employ brominating agents such as elemental bromine, or bromine salts such as sodium bromide inter alia, and hydrogen bromide, preferably in the form of its aqueous solution, hydrobromic acid. Industrial azeotropic mixtures containing hydrobromic acid are particularly preferred.

Examples of oxidizing agents suitable for oxidizing the hydrogen bromide or the bromide ions are peracids, peroxides, hypochlorite (chlorine bleaching solution), chlorine, sodium bromate and potassium peroxodisulfate, and hydrogen peroxide is particularly suitable.

In a preferred embodiment of the novel process, the amounts of oxidizing agents used are such that the hydrogen bromide formed in the reaction is also reoxidized. From 1.5 to 2.0 equivalents of the oxidizing agent are preferably added per bromide equivalent. If, on the other hand, elemental bromine is used as source of bromine, it is sufficient to add from 0.5 to 1.0 equivalent (based on bromine) of an oxidizing agent. It is possible in this way almost to halve the amount of brominating agent employed.

The brominating agent is generally employed in a molar ratio of 0.7–1.3, and preferably in a molar ratio of 0.9–1.0, relative to the o-nitrotoluene II.

A particular advantage of the novel process is that azo compounds such as azo carboxylic esters and azo carbonitriles are used as initiators, and thus irradiation with light can be omitted. These initiators can be dissolved without difficulty in the precursor or in the solvent and accordingly can be present from the outset or metered in. The particularly preferred azo compound is azoisobutyronitrile (AIBN).

The initiators are generally added in a concentration of from 0.1 to 20 mol %, based on the bromine or bromide ion concentration (depending on starting material), and preferably in a concentration of from 1 to 10 mol %, to the reaction mixture.

The bromination is carried out at from 20 to 100° C., preferably 20 to 80° C. The optimal reaction temperature depends, on the one hand, on the thermal stability of the o-nitrotoluene II and the product III obtained therefrom and, on the other hand, on the initiator decomposition temperature. The following table gives a review of various initiators with their structures and 10 h half-life decomposition temperatures. The reaction is preferably carried out slightly above or below the 10 h half-life decomposition temperature of the initiator (±10° C.). Operating below the 10 h half-life decomposition temperature generally results in sparing use of initiator and higher selectivity. However, this result is at the expense of longer reaction times. It is thus possible, by choosing a suitable initiator, for the reaction temperature to be varied within wide limits and adjusted to be optimal for the particular conditions.

the novel process with azo compounds in the presence of oxidizing agents. It may be advantageous in some cases to add a mineral acid, specifically $H_2SO_4$.

The bromination is preferably carried out in a two-phase system. The two-phase system generally comprises the solution of the bromine salt in water or, preferably, the hydrobromic acid together with the solvent and, where appropriate, the initiator or a part-quantity of the initiator. The mixture is brought to the reaction temperature and then the toluene derivative II is metered in, in the presence or absence of the initiator, continuously or in portions over the course of from a half to several hours. The oxidizing agent is metered in parallel with the metering of II generally in such a way that no excess bromine is present in the reaction mixture. It is likewise possible to mix the substrate II with the brominating agent and the initiator and to control the reaction by the metering in of the oxidizing agent.

TABLE

| Designation | Name | Structure | 10 h Half-life decomposition temperature |
|---|---|---|---|
| A | 2,2'-Azobis(4-methoxy-2,4-dimethylvaleronitrile) | 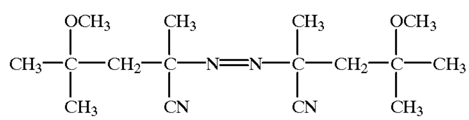 | 30° C. |
| B | 2,2'-Azobis(2-cyclopropylpropionitrile) | 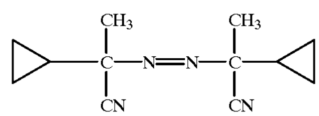 | 42° C. |
| C | 2,2'-Azobis(2,4-dimethylvaleronitrile) | 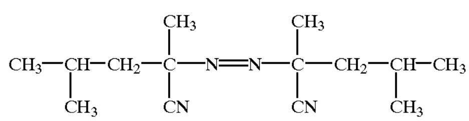 | 51° C. |
| D | 2,2'-Azobis(2-methylpropionitrile) | 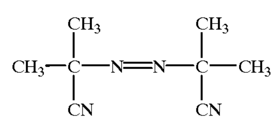 | 65° C. |
| E | Dimethyl 2',2'-azobis(2-methylpropionate) | 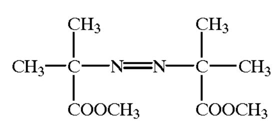 | 66° C. |
| F | 2,2'-Azobis(2-methylbutyronitrile) | 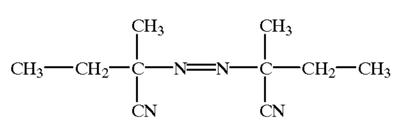 | 67° C. |
| G | 1,1'-Azobis(cyclohexane-1-carbonitrile) | 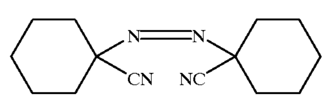 | 88° C. |

As is evident from the table, it is perfectly possible to prepare sensitive compounds which easily decompose by the novel process at mild temperatures in the range from 20 to 50° C., it being necessary to accept somewhat longer reaction times, but it being possible to eliminate the safety risk of an exothermic decomposition. It is surprising that the results obtained with organic peroxides as initiators are worse throughout, whereas very good results are obtained by When bromine is used as source of bromine, the procedure is generally similar to that described above but bromine is metered into water and solvent, with or without initiator. In this procedure, the substrate II can be present from the outset or metered in.

When stable oxidizing agents are used, they can be mixed with the substrate II, and the course of the reaction can be controlled by the addition of the bromine component. When hydrogen peroxide is employed, the latter procedure is generally possible at up to 50° C.

The bromination can be carried out batchwise or, preferably, continuously. The continuous procedure has the advantage that the apparatus is of smaller dimensions and thus the amount of solutions containing the substrate II kept at elevated temperature is less. The pronounced thermal instability of some toluene derivatives II thus means that the continuous process is advantageous in terms of industrial safety.

After the metering in is complete, the reaction mixture is usually kept at the chosen reaction temperature for from 0.5 to 3 hours. Thermally stable benzyl bromides are, as a rule, purified by distillation, while thermally unstable benzyl bromides are further processed in the solution obtained from the novel process.

The novel process is presented by means of examples below:

EXAMPLE 1

Preparation of o-nitrobenzyl bromide a) A solution of 6.6 g (1 mol % based on the hydrobromic acid) of azoisobutyronitrile (AIBN) in 1350 g of chlorobenzene were mixed with 620 g (3.6 mol) of 47% strength hydrobromic acid in a 2.5 liter flat flange flask with impeller stirrer (300 rpm) and baffle. The contents of the reactor were heated to 75° C. After this temperature was reached, feeds I and II were fed in by two metering pumps.

Feed I: A solution of 26.2 g (4 mol %) of AIBN in 548 g (4.0 mol) of ortho-nitrotoluene was introduced continuously over two hours;

Feed II: 725 g (3.2 mol) of 15% strength $H_2O_2$ were introduced in such a way that no excess bromine was present in the solution. About 2.5 hours were required for this.

Stirring was continued at 75° C. for 2 hours after completion of the feeding in, the stirrer was then switched off and the phases were separated at 75° C. 2146.4 g of organic phase were obtained with the following composition (solvent not included):

| | |
|---|---|
| 60.4% | o-nitrobenzyl bromide |
| 21.5% | o-nitrotoluene |
| 18.2% | o-nitrobenzal bromide |

Yield of o-nitrobenzyl bromide: 58.1% based on o-nitrotoluene.

b) 25 g of chlorobenzene in which 13.7 g of o-nitrotoluene and 0.72 g of 2,2'-azobis(4-methoxy-2,4-dimethylvaleronitrile) were dissolved were mixed with 0.24 g of conc. $H_2SO_4$ and 7.8 g of 50% strength $H_2O_2$ at 27° C. in a 250 ml stirred apparatus. While stirring vigorously, 19.7 g of 47% strength hydrobromic acid were added dropwise at 25–27° C. over the course of about 8 hours, stopping the addition of hydrobromic acid if much bromine was released (brown color) and stirring at the reaction temperature until decolorization occurred. GC analysis of the org. phase:

| | |
|---|---|
| 72.7% | o-nitrotoluene |
| 23.9% | o-nitrobenzyl bromide |
| 0.3% | o-nitrobenzal bromide | c) 13.7 g (0.1 mol) of o-nitrotoluene, 25 g of chlorobenzene, 600 mg (2.7 mmol) of V 65 (supplied by Wako; 2,2'-azobis(2,4-dimethylvaleronitrile)), 300 mg of $H_2SO_4$ and 16.4 g (0.15 mol) of 30% strength $H_2O_2$ were mixed at 45° C. 10 g of 47% strength hydrobromic acid were added dropwise over the course of 75 min, and the mixture was stirred at 45° C. for a further 75 min. A further 5 g of hydrobromic acid were added, and the mixture was stirred at room temperature for 12 h. Then 3 g of hydrobromic acid and, in two portions, 5 g and then a further 10 g of a solution of chlorobenzene and V 65 (total 15 g of chlorobenzene +0.86 g (3.9 mmol) of V 65) were added.

Qualitative [sic] HPLC of the org. phase:

| | |
|---|---|
| 56.9% | o-nitrobenzyl bromide |
| 38.4% | o-nitrotoluene |
| 4.7% | o-nitrobenzal bromide | d) 13.7 g of o-nitrotoluene, 25 g of chlorobenzene, 0.58 g of 2,2'-azobis(2,4-dimethylvaleronitrile), 0.24 g of conc. $H_2SO_4$ and 19 g of 47% strength hydrobromic acid were mixed in a 250 ml stirred apparatus and, while stirring vigorously, 60 g of 10% strength aqueous hydrogen peroxide solution were added dropwise over the course of 13 hours. During this, 1 ml portions of a solution consisting of 0.58 g of 2,2'-azobis(2,4-dimethylvaleronitrile) in 10 g of chlorobenzene were added at intervals of one hour to the reaction mixture. The reaction was stopped after 13 hours. GC analysis of the org. phase:

| | |
|---|---|
| 43.9% | o-nitrotoluene |
| 44.2% | o-nitrobenzyl bromide |
| 1.3% | o-nitrobenzal bromide | e) 13.7 g of o-nitrotoluene, 35 g of chlorobenzene, 0.24 g of conc. $H_2SO_4$, 1.74 g of 2,2'-azobis(2,4-dimethylvaleronitrile) and 8.8 g of 30% strength aqueous hydrogen peroxide solution were mixed at 45° C. in a 250 ml stirred apparatus and, while stirring vigorously, 6.6 g of bromine were added dropwise over a period of 24 hours at a rate such that decolorization of the brown solution took place. GC analysis of the org. phase:

| | |
|---|---|
| 52.6% | o-nitrotoluene |
| 38.4% | o-nitrobenzyl bromide |
| 0.9% | o-nitrobenzal bromide | f) 13.7 g of o-nitrotoluene, 38.8 g of chlorobenzene, 0.24 g of conc. $H_2SO_4$ and 19.8 g of 47% strength hydrobromic acid were mixed at 62° C. in a 250 ml stirred apparatus, 2.15 g of 2,2'-azobis(2-methylpropionitrile) were added and, while stirring vigorously, 40 g of chlorine bleaching solution (12.5% active chlorine) were slowly added dropwise over a period of 25 hours. GC analysis of the org. phase

| | |
|---|---|
| 37.4% | o-nitrotoluene |
| 44.4% | o-nitrobenzyl bromide |
| 2.3% | o-nitrobenzal bromide | g) 13.7 g of o-nitrotoluene, 38.8 g of chlorobenzene, 0.24 g of conc. $H_2SO_4$, 19.8 g of 47% strength aqueous hydrobromic acid and 0.72 g of 2,2'-azobis(2-methylpropionitrile) were mixed at 61° C. in a 250 ml stirred apparatus. At this temperature, a solution of 3.27 g of sodium bromate ($NaBrO_3$) in 23 ml of water was added dropwise over the course of 15 hours. GC analysis of the org. phase:

| | |
|---|---|
| 45.7% | o-nitrotoluene |
| 44.8% | o-nitrobenzyl bromide |
| 1.6% | o-nitrobenzal bromide | h) The procedure was as in Example g but at 62–63° C., and instead of $NaBrO_3$ a solution of 17.5 g of potassium peroxodisulfate in 50 ml of water was added to the reaction mixture as oxidizing agent. Workup took place after 20 h. GC analysis of the org. phase:

| | |
|---|---|
| 36.5% | o-nitrotoluene |
| 51.6% | o-nitrobenzyl bromide |
| 2.7% | o-nitrobenzal bromide | i) A solution of 137 g of o-nitrotoluene in 800 ml of chlorobenzene and a solution of 103 g of sodium bromide, 6 g of $Na_2HPO_4$ in 1 l of water were mixed together with 2.5 g of conc. $H_2SO_4$ and 20 g of 2,2'-azobis(2-methylpropionitrile) at 65° C. This two-phase mixture was stirred vigorously while 64 g of chlorine gas ($Cl_2$) were passed in over the course of 2 hours. GC analysis of the org. phase:

| | |
|---|---|
| 34% | o-nitrotoluene |
| 50% | o-nitrobenzyl bromide |
| 4% | o-nitrobenzal bromide | j) 13.7 g of o-nitrotoluene, 38.8 g of chlorobenzene, 0.24 g of conc. $H_2SO_4$ and 19.8 g of 47% strength aqueous hydrobromic acid were mixed at 62° C. in a 250 ml stirred apparatus, 2.32 g of 2,2'-azobis(2-methylpropionitrile) were added and, while stirring vigorously, 11.6 g of peroxyacetic acid (32% strength) were added dropwise in small portions over the course of 25.5 hours.

GC analysis of the org. phase:

| | |
|---|---|
| 53.5% | o-nitrotoluene |
| 32.2% | o-nitrobenzyl bromide |
| 0.5% | o-nitrobenzal bromide |

EXAMPLE 2

Preparation of 3-chloro-2-bromobenzyl bromide 267.7 g of 2-bromo-3-chlorotoluene, 530 g of chlorobenzene, 2.5 g of conc. $H_2SO_4$, 257.9 g of 47% strength hydrobromic acid and 14 g of 2,2'-azobis(2-methylpropionitrile) were mixed at 63° C. in a 2 l stirred apparatus. 332.3 g of a 10% strength aqueous hydrogen peroxide solution were added dropwise over the course of one hour and 25 minutes, and then the mixture was stirred at 63° C. for 30 minutes. GC analysis of the org. phase:

| | |
|---|---|
| 32.2% | 3-chloro-2-bromotoluene |
| 56.5% | 3-chloro-2-bromobenzyl bromide |
| 4.2% | 3-chloro-2-bromobenzal bromide |

These 3 components could be separated and purified by distillation without difficulty.

EXAMPLE 3

Preparation of 3-methyl-2-bromobenzyl bromide 104.5 g of 2-bromo-m-xylene(2,6-dimethylbromobenzene), 200 g of chlorobenzene, 1 g of conc. $H_2SO_4$, 87.2 g of 47% strength hydrobromic acid and 6 g of 2,2'-azobis(2-methylpropionitrile) were mixed at 63° C. in a 1 l stirred apparatus. 75 g of 10% strength aqueous hydrogen peroxide solution were added dropwise over the course of 30 minutes, and the mixture was stirred at 64° C. for 25 minutes.

| | |
|---|---|
| 40.7% | 2,6-dimethylbromobenzene |
| 45.8% | 3-methyl-2-bromobenzyl bromide |
| 0.6% | 3-methyl-2-bromobenzal bromide |
| 3.0% | 2,6-bis-(bromomethyl)bromobenzene |

Once again, the benzyl bromide component could be removed and obtained in pure form by distillation.

EXAMPLE 4

Preparation of 4-chloro-2-fluorobenzyl bromide 361.5 g of 4-chloro-2-fluorotoluene, 520 g of chlorobenzene, 6 g of conc. $H_2SO_4$, 467 g of 47% strength hydrobromic acid and 2.7 g of 2,2'-azobis(2-methylpropionitrile) were mixed at 70° C. in a 4 l stirred apparatus. 620.5 g of a 10% strength aqueous hydrogen peroxide solution and a solution of 16.5 g of 2,2'-azobis(2-methylpropionitrile) in 270 g of chlorobenzene were simultaneously added dropwise over the course of 1.5 hours. The mixture was then stirred at 70° C. for 1 hour. GC analysis of the org. phase:

| | |
|---|---|
| 31.2% | 4-chloro-2-fluorotoluene |
| 60.5% | 4-chloro-2-fluorobenzyl bromide |
| 4.3% | 4-chloro-2-fluorobenzal bromide |

In this case too, purification was possible by fractional distillation.

EXAMPLE 5
Preparation of methyl 2,4-dichloro-3-(bromomethyl)benzoate 94.6 g of methyl 2,4-dichloro-3-methylbenzoate, 315 g of chlorobenzene, 1 g of conc. $H_2SO_4$, 85.5 g of 47% strength hydrobromic acid and 3.5 g of 2,2'-azobis(2-methylpropionitrile) were mixed at 63° C. in a 1 1 stirred apparatus. Then, at temperatures from 63 to 68° C., 73.5 g of 10% strength aqueous hydrogen peroxide solution were added over the course of 35 minutes. The mixture was stirred at the reaction temperature for 2 hours and then a further 73.5 g of 10% strength hydrogen peroxide solution were added dropwise over the course of 30 minutes, a further 1.5 g of 2,2'-azobis(2-methylpropionitrile) were added to the reaction, the mixture was stirred at the reaction temperature for 2 hours and 35 minutes, and finally 36.8 g of 10% strength hydrogen peroxide solution were added dropwise at 63–67° C. over the course of 15 minutes, the mixture was stirred at the reaction temperature for a further 2 hours and cooled to room temperature, and the organic phase was separated off. The chlorobenzene solution contained the required product methyl 2,4-dichloro-3-bromomethylbenzoate in a purity of 96.1% (according to HPLC analysis ignoring solvent).

We claim:

1. A process for preparing substituted benzyl bromides of the formula I

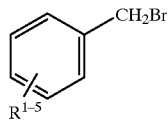

I where at least one substituent $R^{1-5}$ is an electron-attracting group comprising fluorine, chlorine, bromine, $C_1$–$C_4$-alkoxycarbonyl, cyano or nitro, and the other substituents $R^{1-5}$ are hydrogen or methyl, by bromination of substituted toluenes of the formula II

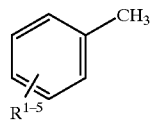

II with a brominating agent selected from the group consisting of: bromine, bromine salts and hydrogen bromide, optionally in the form of its aqueous solution, at from 20 to 95° C., wherein the bromination is carried out in the presence of an azo carbonitrile or of an azo carboxylic ester and in the presence of an oxidizing agent.

2. A process as claimed in claim 1, wherein from 0.5 to 1 equivalent of an oxidizing agent is employed in the case of elemental bromine as brominating agent, and from 1.5 to 2 equivalents of an oxidizing agent are employed in the case of bromides or hydrogen bromide.

3. A process as claimed in claim 1, wherein hydrogen peroxide, peracetic acid, chlorine, sodium hypochlorite, sodium bromate or potassium peroxydisulfate are used as oxidizing agent.

4. A process as claimed in claim 1, wherein hydrogen peroxide is used as oxidizing agent and is initially present together with the substrate to be brominated at up to 50° C.

5. A process as claimed in claim 1, wherein the bromination is carried out in a two-phase system.

6. A process as claimed in claim 1, wherein the bromination is carried out continuously.

* * * * *